United States Patent [19]

Downs, II

[11] 4,193,028

[45] Mar. 11, 1980

[54] EDDY CURRENT INSTRUMENTATION CIRCUITRY FOR DISTINGUISHING FLAW SIGNALS FROM SPURIOUS NOISE SIGNALS

[75] Inventor: Byron E. Downs, II, Hopkins, Minn.

[73] Assignee: Honeywell Inc., Minneapolis, Minn.

[21] Appl. No.: 903,268

[22] Filed: May 5, 1978

[51] Int. Cl.² ............................................. G01R 33/00
[52] U.S. Cl. ...................................... 324/237; 307/360
[58] Field of Search ............................... 324/217–221, 324/228, 233, 234, 236, 237–241, 262, 173, 174, 175; 307/360, 232; 328/120, 146, 147

[56] References Cited

U.S. PATENT DOCUMENTS

| | | | |
|---|---|---|---|
| 2,109,455 | 3/1938 | Barnes et al. | 324/241 |
| 2,511,564 | 5/1950 | Callan | 324/240 |
| 2,614,154 | 10/1952 | Dionne | 324/217 |
| 2,617,854 | 11/1952 | Van Valkenburg | 324/240 |
| 2,657,355 | 10/1953 | Dionne | 324/217 |
| 2,869,073 | 1/1959 | McKee et al. | 324/217 |
| 2,948,848 | 8/1960 | Arnelo | 324/238 |
| 2,980,848 | 4/1961 | Pratt et al. | 324/238 |
| 3,273,055 | 9/1966 | Quittner | 324/240 |
| 3,437,917 | 4/1969 | Gunkel et al. | 324/226 |
| 3,955,102 | 5/1976 | Chi | 307/360 |
| 4,095,179 | 6/1978 | Bremer et al. | 324/173 |

FOREIGN PATENT DOCUMENTS 2514135  10/1975  Fed. Rep. of Germany ........... 324/228

Primary Examiner—Rudolph V. Rolinec
Assistant Examiner—Walter E. Snow
Attorney, Agent, or Firm—John P. Sumner

[57] ABSTRACT

An electronic circuit to be used in conjunction with eddy current non-destructive flaw detection instrumentation for distinguishing from noise or other undesirable signals a flaw signal having a characteristic frequency and a negative excursion followed by a positive excursion. The circuit includes two channels, each of which comprises a threshold detector, a differentiator, a filter, and a variable pulse width one-shot multivibrator, each of which receives the characteristic signal. One channel processes the negative excursion, and the other channel processes the positive excursion. Each channel produces a pulse of predetermined time duration if the excursion being processed exceeds a predetermined threshold. The leading edge of the pulse produced in association with the negative excursion corresponds in time to the time at which the trailing positive going edge of the negative excursion crosses a predetermined negative threshold. The leading edge of the pulse produced in association with the positive excursion corresponds in time to the time at which the leading positive going edge of the positive excursion crosses a predetermined positive threshold. By way of an AND gate connected to both channels, the circuit produces an output signal indicating a flaw only if the pulses produced in each channel coexist in time.

7 Claims, 3 Drawing Figures

EDDY CURRENT INSTRUMENTATION CIRCUITRY FOR DISTINGUISHING FLAW SIGNALS FROM SPURIOUS NOISE SIGNALS

BACKGROUND OF THE INVENTION

1. Field of the Invention

This invention relates to eddy current instrumentation used for non-destructive flaw detection testing and, more particularly, to distinguishing in such testing noise or other undesirable signals from a signal indicating a flaw.

2. Description of the Prior Art

Commercially available eddy current instrumentation is available for use in non-destructive flaw detection testing. Examples of such instrumentation are Models 730-I and 730-II made by K. J. Law Associates, Inc., 26325 West Eight Mile Road, Detroit, Mich. 48240.

In such testing relative motion is commonly established between a self-comparison differential probe and the material under test. Each time such a probe passes over a flaw in the material, a signal is generated by the probe.

The signal generated in response to a flaw typically has a dual polarity characteristic waveform comprising a negative excursion leading a positive excursion, a frequency related to the relative speed between the material (or flaw) and the probe, and an amplitude related to the size of the flaw.

In its commercially available form, the eddy current test instrumentation indicates a flaw whenever it receives from the probe a signal exceeding a predetermined threshold. This threshold is related to and can be adjusted for the nominal minimum flaw size to be detected.

A problem with such instrumentation is that noise signals will frequently exceed the threshold necessary for adequate flow resolution with the result that flaws are incorrectly indicated and parts or materials are unnecessarily rejected.

SUMMARY OF THE INVENTION

The present invention virtually eliminates the problem of noise induced errors. The invention is a circuit which includes a single input terminal connected through a filter to each of two channels. Each channel comprises four primary components connected in series. Listed in order from channel input to channel output, the primary components of each channel are a threshold detector, a differentiator, a filter, and a variable pulse width one-shot multivibrator ("one-shot"). The threshold detector in one channel is a negative threshold detector, while the threshold detector in the other channel is a positive threshold detector. The output of one channel is connected to one input of a two-input AND gate, and the output of the other channel is connected to the other input of the AND gate. The output of the AND gate is connected to a single output terminal.

Each channel of the circuit receives at its input the previously described characteristic signal generated by the probe. The channel including the negative threshold detector processes the negative excursion of the signal, and the channel including the positive threshold detector processes the positive excursion of the signal.

A pulse of predetermined time duration is produced by a channel if the signal being processed exceeds a predetermined threshold. The leading edge of the pulse produced in association with the negative excursion corresponds in time to the time at which the trailing positive going edge of the negative excursion crosses a predetermined negative threshold. The leading edge of the pulse produced in association with the positive excursion corresponds in time to the time at which the leading positive going edge of the positive excursion crosses a predetermined positive threshold. By way of the AND gate connected to the output of each channel, the circuit produces an output only if the signals produced in each channel coexist in time at the inputs of the AND gate.

In this manner, the present invention can correctly identify signals associated with flaws. In addition, the invention rejects most noise signals which rarely include both negative and positive excursions that are of sufficient amplitude and that are connected by a transition having a sufficiently short rise time.

Accordingly, the invention vastly improves the reliability of existing eddy current instrumentation used for non-destructive flaw detection testing. In addition, since flaw signal thresholds can be set within noise levels, the invention improves the sensitivity of such instrumentation.

DESCRIPTION OF THE PREFERRED EMBODIMENT

Structure

In the preferred embodiment, the circuitry of the present invention was successfully used with the previously indicated instrumentation models. Such instrumentation includes a differential amplifier to amplify the signals generated by the probe. The circuitry of the invention is placed between this differential amplifier and the rest of the instrumentation electronics.

Figure 1:
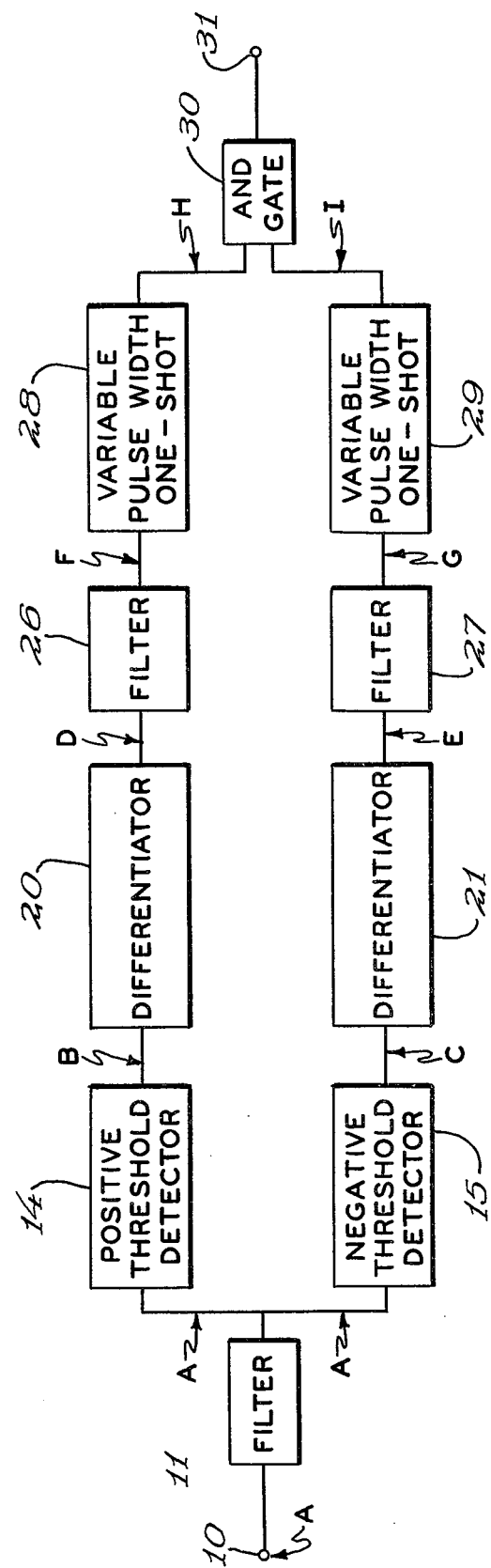
FIG. 1 is a block diagram illustrating the preferred embodiment of the present invention.

Referring now more particularly to FIG. 1 and to the details of the present invention, the circuit includes at an input terminal 10 the input of a filter 11. The output of filter 11 is connected to the inputs of threshold detectors in each of two channels each comprising four primary components connected in series.

The primary components of one channel, listed in order from channel input to channel output, are a negative threshold detector 15, a differentiator 21, a filter 27, and a variable pulse width one-shot 29. The primary components of the other channel, also listed in order from channel input to channel output, are a positive threshold detector 14, a differentiator 20, a filter 26, and a variable pulse width one-shot 28.

The output of one channel is connected to one input of a two-input AND gate 30, and the output of the other channel is connected to the other input of AND gate 30. The output of AND gate 30 is connected to a circuit output terminal 31.

Figure 2:
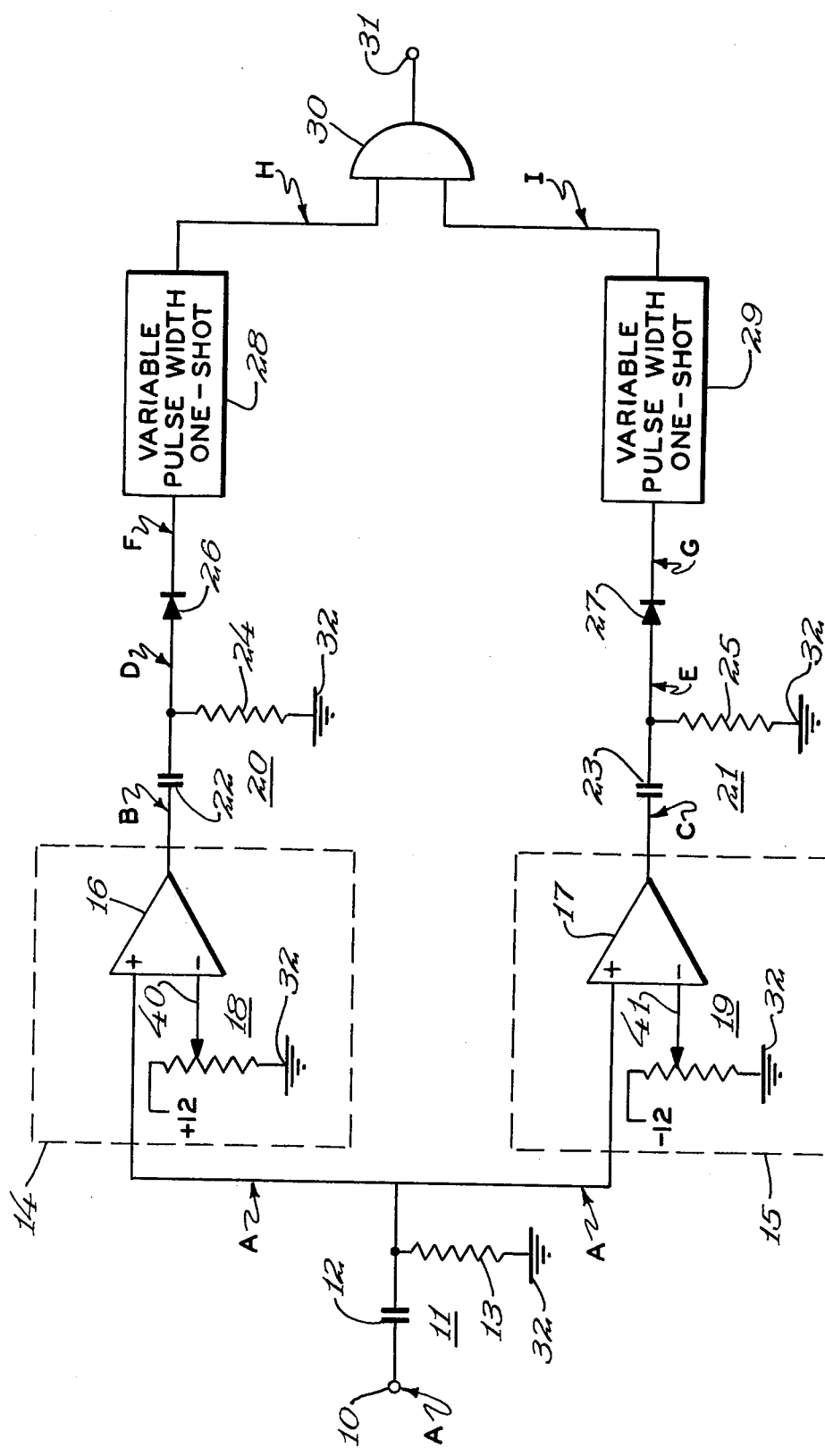
FIG. 2 is a schematic drawing illustrating in greater detail the preferred embodiment set forth in FIG. 1.

Referring now to the schematic drawing of FIG. 2, it can be seen that filter 11 includes a capacitor 12 which is connected between input terminal 10 and one side of a resistor 13, the other side of which is connected to ground 32. The ungrounded side of resistor 13 is also at the output of filter 11 which, as previously indicated, is connected to the input of negative threshold detector 15 and to the input of positive threshold detector 14.

The input of negative threshold detector 15 is the positive input of a voltage comparator/buffer 17. The negative input of voltage comparator/buffer 17 is connected to a wiper 41 of a potentiometer 19 which is connected between a negative 12 volts and ground 32.

Similarly, the input of positive threshold detector 14 is the positive input of a voltage compartor/buffer 16. The negative input of comparator/buffer 16 is connected to a wiper 40 of a potentiometer 18 which is connected between a positive 12 volts and ground 32.

Voltage comparator/buffers 16 and 17 are conventional and may be, for example, LM 311's.

Differentiator 21 comprises a capacitor 23 and a resistor 25 with capacitor 23 connected between the output of voltage comparator/buffer 17 and one end of resistor 25, the other end of which is connected to ground 32.

Likewise, differentiator 20 comprises a capacitor 22 and a resistor 24 with capacitor 22 connected between the output of voltage comparator/buffer 16 and one end of resistor 24, the other end of which is connected to ground 32.

Filter 27 comprising a diode is connected for forward current flow from the ungrounded end of resistor 25 to the input of variable pulse width one-shot 29, while filter 26 comprising a diode is connected for forward current flow from the ungrounded end of resistor 24 to the input of variable pulse width one-shot 28.

Variable pulse width one-shot 29 has its output connected to one input of two-input AND gate 30, while variable pulse width one-shot 28 has its output connected to the other input of AND gate 30.

The output of AND gate 30 is connected to circuit output terminal 31.

Operation

Figure 3:
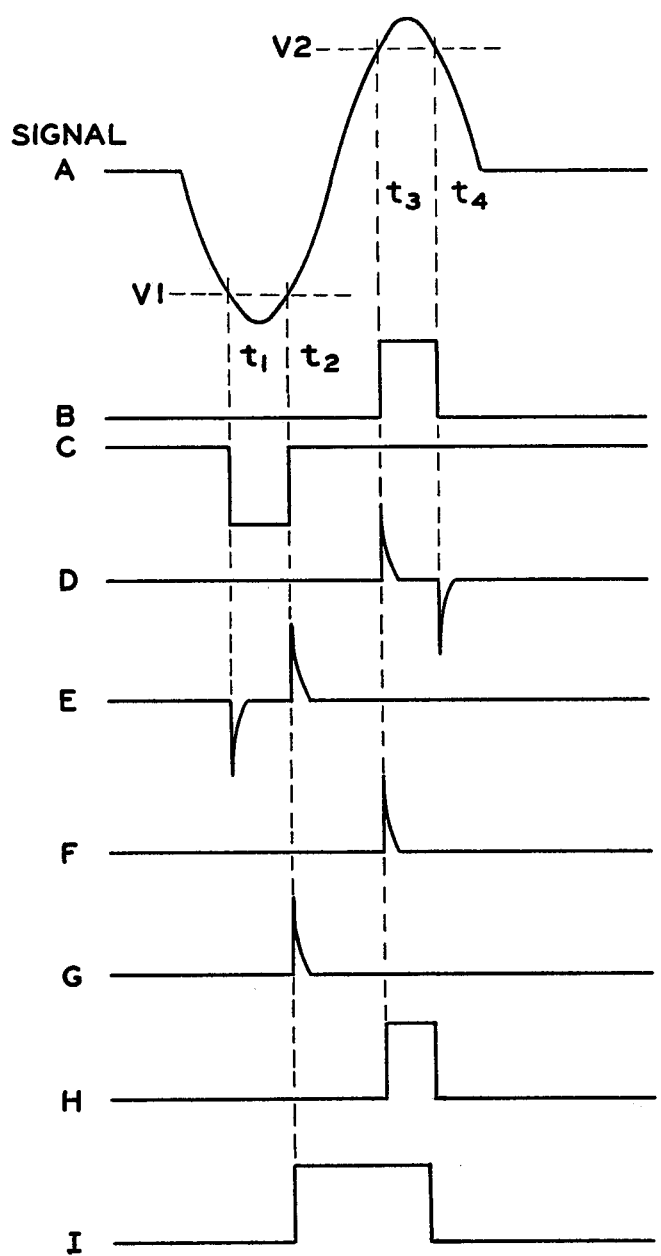
FIG. 3 illustrates signals appearing at various points in the circuit of FIGS. 1 and 2.

Signal A in FIG. 3 illustrates the signal typically generated by the self comparison differential probe when a flaw is encountered in the material under test. Whether the negative or the positive excursion of this signal occurs first is determined by the orientation of the probe with respect to the direction of relative motion between the material under test and the probe. Although arbitrary, the signal phase illustrated at A in FIG. 3 with the negative excursion leading the positive excursion was selected for the design of the preferred embodiment of the present invention. Thus, in applying the preferred embodiment of the present invention, the probe is oriented with respect to the direction of relative motion between the material under test and the probe such that the negative excursion occurs prior to the positive excursion.

Filter 11 passes signal A but blocks any nominal D.C. voltage level that may be present.

Threshold detectors 14 and 15 operate as switches with negative threshold detector 15 always passing a positive 12 volts except when voltage comparator/buffer 17 sees a negative signal of amplitude greater than the threshold established by potentiometer 19 and with positive threshold detector 14 passing a positive 12 volts only when voltage/comparator buffer 16 sees a positive signal of amplitude greater than the threshold established by potentiometer 18. In this manner, threshold detectors 14 and 15 each pass squarewave signals with durations corresponding to the time that the incoming signals exceed the thresholds established.

In this regard, signal C in FIG. 3 corresponds to the signal appearing at the output of negative threshold detector 15 whenever the negative excursion of signal A exceeds negative threshold V1 established by potentiometer 19. Signal C is a negative going squarewave falling from a positive 12 volts to ground and rising back to a positive 12 volts. The leading edge of signal C occurs at time $t_1$, the time at which the negative excursion of signal A first exceeds negative threshold V1. The trailing edge of signal C occurs at time $t_2$, the time at which the negative excursion of signal A first returns to negative threshold V1.

Similarly, signal B corresponds to the signal appearing at the output of positive threshold detector 14 whenever the positive excursion of signal A exceeds positive threshold V2 established by potentiometer 20. Signal B is a positive going squarewave rising from ground to a positive 12 volts and falling back to ground. The leading edge of signal B occurs at time $t_3$, the time at which the positive excursion of signal A first exceeds positive threshold V2. The trailing edge of signal B occurs at time $t_4$, the time at which the positive excursion of signal B first returns to positive threshold V2.

Differentiator 21 and filter 27 provide signal processing means between negative threshold detector 15 and variable pulse width one-shot 29, while differentiator 20 and filter 26 provide signal processing means between positive threshold detector 14 and variable pulse width one-shot 28.

Differentiator 21 differentiates signal C into signal E comprised of a first negative going pulse having its leading edge occurring at time $t_1$ and a second positive going pulse having its leading edge occurring at time $t_2$.

In a similar manner, differentiator 20 differentiates signal B into signal D comprised of a first positive going pulse having its leading edge occurring at time $t_3$ and a second negative going pulse having its leading edge occurring at time $t_4$.

Filter 27 transforms signal E into signal G having its leading edge at time $t_2$ by permitting the positive going pulse of signal E to pass while precluding passage of the negative going pulse of signal E. In like manner, filter 26 transforms signal D into signal F havings its leading edge at time $t_3$ by permitting the positive going pulse of signal D pulse to pass while precluding passage of the negative going pulse of Signal D. Therefore, only signal G with its leading edge at time $t_2$ appears at the output of filter 27 and only signal F with its leading edge at time $t_3$ appears at the output of filter 26.

Variable pulse width one-shots 28 and 29 are pulse generating means which are well known to those skilled in the art. Each time variable pulse width one-shot 29 receives signal G at its input, positive going signal I appears at its output. Signal I is a squarewave having its leading edge at time $t_2$ and having an adjustable duration which is predetermined by variable pulse width one-shot 29.

Similarly, each time variable pulse width one-shot 28 receives signal F at its input, positive going signal H appears at its output. Signal H is a squarewave having its leading edge at time $t_3$ and having an adjustable duration which is predetermined by variable pulse width one-shot 28.

With regard to variability of duration, signal I occurring at time $t_2$ is adjustable from approximately 0.3 millisecond to approximately 50 milliseconds, while signal H occurring at time $t_3$ is adjustable from approximately 0.2 millisecond to approximately 34 milliseconds.

AND gate 30 operates as a comparison means by providing an output only if it concurrently receives signals from both variable pulse width one-shots 28 and 29. Thus, if signals H and I coexist in time, an output signal will appear at the output of AND gate 30 at circuit output terminal 31.

Further reference to the signals illustrated in FIG. 3 may lead to a better understanding of the present invention. As previously explained and as illustrated in FIG. 3, the leading edge of signal I occurs at time $t_2$, the time at which the negative excursion of signal A first returns to negative threshold V1. Similarly, the leading edge of signal H occurs at time $t_3$, the time at which the positive excursion of signal A first exceeds positive threshold V2.

Accordingly, no output signal will appear at output terminal 31 unless input terminal 10 receives a dual polarity signal which includes a positive going transition rising through negative threshold V1 (adjusted with potentiometer 19) and rising through positive threshold V2 (adjusted with potentiometer 18) within the duration of signal I (predetermined by variable pulse width one-shot 29).

In this manner, a signal appearing at output terminal 31 of the present invention represents a flaw in the material under test.

The embodiments of the invention in which an exclusive property or right is claimed are defined as follows:

1. In an apparatus for eddy current non-destructive testing of materials wherein means are provided for obtaining relative motion between the material and a probe capable of detecting a flaw in such material and in response to each such flaw generating an electrical output signal having a characteristic frequency and both first and second polarity excursions, means for improving apparatus signal detection sensitivity and its ability to reliably distinguish signals representing material flaws from spurious noise signals, the means comprising:

a first threshold detector having an input connected to receive signals from the probe and an output for providing an output signal whenever the amplitude of a signal at its input exceeds a predetermined threshold of first polarity;

a second threshold detector having an input connected to receive signals from the probe and an output for providing an output signal whenever the amplitude of a signal at its input exceeds a predetermined threshold of second polarity;

first and second pulse generating means with the first pulse generating means having an input connected to receive the output signal from the first threshold detector, the first pulse generating means further having an output for providing a pulse of a predetermined time duration in response to each signal received from the output of the first threshold detector, and with the second pulse generating means having an input connected to receive the output signal from the second threshold detector, the second pulse generating means further having an output for providing a pulse of a predetermined time duration in response to each signal received from the output of the second threshold detector where the pulses of predetermined time duration coexist at some point in time; and comparison means having first and second inputs for receiving pulses from the outputs of the first and second pulse generating means respectively, the comparison means further having an output for providing a signal whenever pulses appear simultaneously at both of its inputs, the signal at the output of the comparison means being representative of a flaw in the material under test.

2. Apparatus according to claim 1
wherein the first polarity excursion of the electrical output signal occurs prior to the second polarity excursion of the electrical output signal;
wherein first signal processing means are connected between the first threshold detector and the first pulse generating means, the first signal processing means providing at an output a pulse having a leading edge which corresponds in time to the trailing edge of the signal received from the first threshold detector; and
wherein second signal processing means are connected between the second threshold detector and the second pulse generating means, the second signal processing means providing at an output a pulse having a leading edge which corresponds in time to the leading edge of the signal received from the second threshold detector.

3. Apparatus according to claim 1 wherein the pulse generating means each include means for adjusting the predetermined time durations of the pulse provided at the outputs of the pulse generating means.

4. Apparatus according to claim 1 wherein the predetermined time duration of the pulses provided at the output of the first pulse generating means ranges from approximately 0.3 millisecond to approximately 50 milliseconds while the predetermined time duration of the pulses provided at the output of the second pulse generating means ranges from approximately 0.2 millisecond to approximately 34 milliseconds.

5. Apparatus according to claim 4 wherein the predetermined time durations are variable.

6. Apparatus according to claim 1 wherein the first and second threshold detectors each include means for adjusting the predetermined thresholds.

7. Apparatus according to claim 1 wherein a filter is connected between the probe and the inputs of the first and second threshold detectors.

* * * * *